United States Patent [19]

Harvey

[11] Patent Number: 4,888,484

[45] Date of Patent: Dec. 19, 1989

[54] APPARATUS AND METHOD FOR SPECTROPHOTOMETRIC ANALYSIS OF A MATERIAL IN A MOVING PROCESS STREAM

[75] Inventor: Robert J. Harvey, Charlotte, N.C.

[73] Assignee: Automatik Machinery Corporation, Charlotte, N.C.

[21] Appl. No.: 139,964

[22] Filed: Dec. 31, 1987

Related U.S. Application Data

[63] Continuation-in-part of Ser. No. 831,296, Feb. 20, 1986, Pat. No. 4,717,827.

[51] Int. Cl.$^4$ ............................................. G01N 21/35
[52] U.S. Cl. .................................... 250/343; 356/434; 356/436; 356/440
[58] Field of Search ..................... 250/343, 373, 345; 356/246, 436, 440, 435, 434

[56] References Cited

U.S. PATENT DOCUMENTS

| | | | |
|---|---|---|---|
| 2,690,695 | 10/1954 | Coates | 88/14 |
| 2,885,863 | 5/1959 | Berger | 62/32 |
| 3,177,706 | 4/1965 | Shuman et al. | 73/61 |
| 3,521,958 | 7/1970 | Treharne | 356/84 |
| 3,582,222 | 6/1971 | Hoblik | 356/246 |
| 3,606,547 | 9/1971 | Iwahashi | 356/97 |
| 3,614,243 | 10/1971 | Harvey | 356/246 |
| 3,646,313 | 2/1972 | Gorgone et al. | 219/200 |
| 3,658,422 | 4/1972 | Wilkinson | 356/89 |
| 3,684,386 | 8/1972 | Noll | 365/246 |
| 3,781,115 | 12/1973 | Jones | 365/180 |
| 3,877,817 | 4/1975 | Ralston | 356/319 |
| 3,886,364 | 5/1975 | Walker et al. | 250/343 |
| 4,023,909 | 5/1977 | Ross | 356/205 |
| 4,197,088 | 4/1980 | Meserol et al. | 23/230 |
| 4,283,142 | 8/1981 | De Steur et al. | 356/319 |
| 4,305,663 | 12/1981 | Perkins et al. | 356/323 |
| 4,307,960 | 12/1981 | Barlow et al. | 365/323 |
| 4,367,043 | 1/1983 | Sweet et al. | 356/338 |
| 4,455,097 | 6/1984 | Ichikawa et al. | 356/323 |
| 4,458,323 | 7/1984 | Willis et al. | 364/582 |
| 4,484,815 | 11/1984 | Akiyama et al. | 356/325 |
| 4,529,306 | 7/1985 | Kilham et al. | 356/237 |
| 4,545,681 | 10/1985 | Watanabe | 356/325 |
| 4,577,106 | 3/1986 | Fukasawa et al. | 250/347 |
| 4,583,853 | 4/1986 | Maeda et al. | 356/323 |
| 4,657,390 | 4/1987 | Doyle | 356/346 |
| 4,739,167 | 4/1988 | Riegler | 250/343 |
| 4,770,530 | 9/1988 | Van Aken et al. | 356/323 |

FOREIGN PATENT DOCUMENTS

| | | |
|---|---|---|
| 2133797 | 1/1973 | Fed. Rep. of Germany ...... 356/436 |
| 57-147059 | 9/1982 | Japan . |
| 59-9545 | 1/1984 | Japan . |
| 13246 | 1/1985 | Japan ................................. 250/343 |
| 667896 | 3/1952 | United Kingdom . |
| 1305214 | 1/1973 | United Kingdom . |

OTHER PUBLICATIONS

Variable Path Length Infrared Cell for Use at Elevated Temperatures, vol. 23—Dept. of Organic Chemistry, LaTrobe Univ., (10/23/73), pp. 282–283.

(List continued on next page.)

Primary Examiner—Carolyn E. Fields
Attorney, Agent, or Firm—W. Thad Adams, III

[57] ABSTRACT

An apparatus and method for spectrophotometric analysis of material in a moving process stream wherein the material is directed into an observation chamber within a sample cell and exposed to a radiation beam suitable for spectrophotometric purposes. A radiation source and a radiation detector are contained within a first compartment and a second compartment environmentally isolated from the first compartment and within which the sample cell is contained. Reflectors are positioned within the second compartment for receiving the radiation beam from the first compartment, directing the radiation beam through the sample cell and the material to be analyzed contained therein, and directing the radiation beam back into the second compartment and the radiation detector positioned therein. The second compartment maintains the environment therein within a range acceptable for radiation analysis of the material within the sample cell. Mirrors are positioned within the second compartment for diverting the radiation beam from passage through the material and for determining a reference spectrum within the same environment as the sample cell and directing the diverted beam to the radiation detector.

7 Claims, 4 Drawing Sheets

OTHER PUBLICATIONS

Sampling Method Makes On-Stream IR Analysis Work, (Sep. 1982), Paul A. Wilkes—General Analysis Corp.

Evolution of FTIR from the Laboratory to the Production Environment, (Dec. 1985), Clark Hewitt, K. S. Morris and A. J. Rein—pp. 32, 34–39.

FTIR Analyzer for Real-Time Multicomponent Analysis, (Dec. 1985), Mark S. Roth and David O'Donnell-Leach—pp. 40, 43, 45–48, 51–52.

On-Line Monitoring System for Beverage Packaging Lines, (Dec. 1985), Paul Wilks—pp. 76–78.

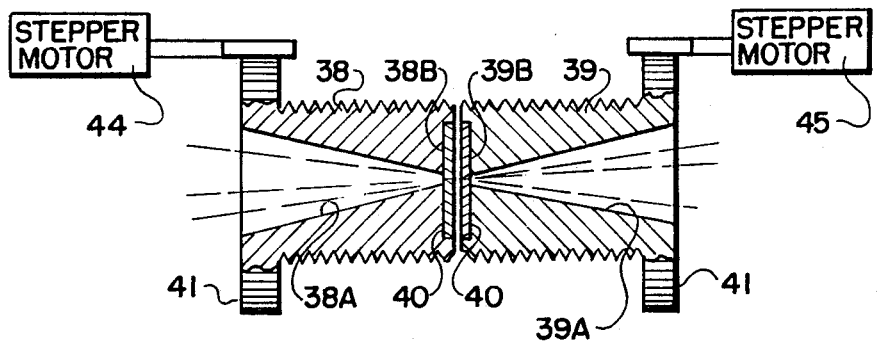
FIG. 4
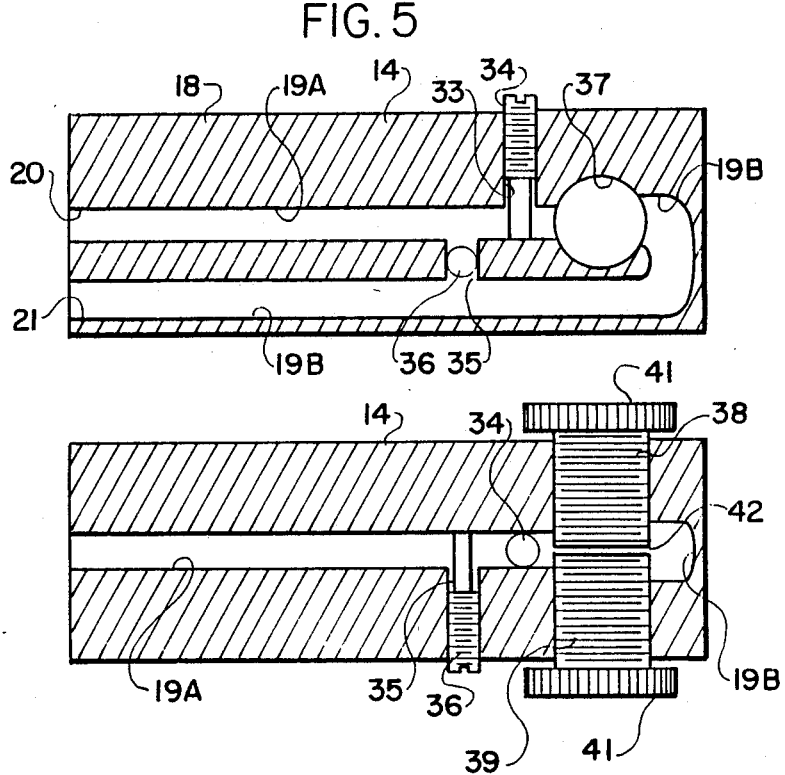
FIG. 5
FIG. 6

APPARATUS AND METHOD FOR SPECTROPHOTOMETRIC ANALYSIS OF A MATERIAL IN A MOVING PROCESS STREAM

This application is a continuation-in-part of application Ser. No. 831,296 filed on February 20, 1986, now U.S. Pat. No. 4,717,827.

TECHNICAL FIELD AND BACKGROUND OF THE INVENTION

This invention relates to a method and apparatus for spectrophotometric chemical analysis of a material contained within a moving stationary process stream. The invention described in this application is intended specifically to be used on-line in a manufacturing or other process environment where rapid analysis of the chemical composition of a material in a moving process stream is critical to efficient and economical quality control. The invention desclosed in this application has a very wide range of use. For purposes of description and illustration, the spectrophotometric apparatus uses infrared form of radiation in order to obtain an infrared spectrum for analysis according to the Fourier Transform Infrared Spectroscopy method. In this application this is referred to as "FTIR."

While chemical analysis of a wide range of materials is possible, the invention will be described for purposes of illustration with relation to the chemical analysis of a polymer melt contained and moving in a process stream such as in a polymer manufacturing facility or in a synthetic fiber manufacturing facility.

The infrared frequency range (2.5 to 50 microns or 4,800 to 200 wave numbers) has been used in infrared spectroscopy for some time. The popularity of FTIR infrared radiation analysis as an analytical tool is the result of the relatively large amount of information that infrared spectroscopy provides and the manner in which it can be generated and analyzed. It is most widely used for the identification of all organic compounds and many non-organic compounds, and is useful because it can analyze a sample whether in the solid, liquid molten or gas phase and whether the materials are pure or impure. Depending on the manner of use, both qualitative and quantitative information can be provided. Analysis of infrared radiation output data is relatively rapid, lending itself to at least theoretical use in on-line processes. However, the physical problems associated with testing of materials in an on-line environment have been difficult. Accordingly, most infrared analysis has been and still is conducted in a laboratory environment. In the polymer manufacturing and processing environment described above, the typical method of qualitative analysis of the polymer melt is to take a sample from the end product, i.e., flake or pellet and deliver it to a laboratory location for infrared analysis. This procedure is particularly unsuitable because of the nature of the polymer manufacturing process. Polymers, such as polypropylene, polyethylene, nylon and the like are produced from the reaction of various organic compounds at very high temperatures and pressures on the order of approximately 572° F. (300° C. and 2500 psi), (1,757,750 kg/m$^2$). Maintenance of this temperature and pressure throughout the process stream is essential, since the polymer very quickly hardens into a virtually indestructible mass upon cooling. For this reason, polymer manufacturing facilities typically run twenty-four hours a day, seven days a week for several months. Therefore, a polymer manufacturing plant of relatively modest size will manufacture polymer in huge quantities. The many different uses for polymers require that they be manufactured according to many varying formulas. A typical polymer will contain several primary constituent parts and many secondary additives, often in minute quantities, which nevertheless have a significant affect on the qualities of the end product. For example, in polymers such as polyester and nylon, additives to the polymer mix reduce the coefficient of friction of yarn manufactured from the polymer so that yarn guides, rings and the like which come into contact with the rapidly moving yarn do not wear out rapidly. Other additives and formulation end groups in the polymer control the rate and extent to which the polymer absorbs and reacts with dyes. Still other additives affect the strength, elongation, moisture absorption rate and many other characteristics. Infrared analysis of polymer is typically carried out by forming a film or melt from polymer flake or pellets. The film or melt is allowed to cool and, when analyzed in the laboratory, is analyzed in its cool state. Infrared analysis of polymer at ambient temperature gives results which may differ considerably from analysis of the same polymer at its process stream temperature. This limits the utility of the information obtained. Even if the polymer melt is reheated, the results will still not provide a completely accurate reflection of the polymer melt in the process stream since, each time the polymer melt is heated, cooled and reheated, its chemical composition changes somewhat due to heat related reaction of the polymer components and the escape of volatile from the polymer caused by heating. Even if reasonably accurate results are achieved, the length of time which necessarily elapses between the taking of the sample, the completion of the infrared analysis in the laboratory and the correction of the formula can result in the manufacture of vast quantities of polymer which exceed quality control limitations and must be reprocessed, thrown away or sold as waste or second quality product.

Therefore, it is highly desirable to sample and carry out infrared radiation analysis of materials such as polymers on an on-line basis at the process stream.

It is necessary to maintain a polymer melt at its process stream temperature during FTIR analysis. Even momentary contact by the polymer stream with a relatively cooler object such as the probe will cause a relatively thick film or coating of polymer to form and cling to the probe. Thereafter, the infrared radiation is only sampling the stationary material clinging to the probe to a depth of 4 to 8 microns and not the material in the moving process stream.

The development of a sample cell which permits on-line chemical analysis of polymer melt in a moving process stream permits samples to be taken and quality variations detected with sufficient speed so that corrections can be made before significant amounts of waste or second quality polymers are produced. Furthermore, the development of such a sample cell permits the continuous sampling of the polymer melt. Such a continuous process permits the establishment of alarm limits which automatically alerts production personnel when the chemical composition of the polymer melt varies outside of specifications, diverts defective polymer melt out of the process stream for reprocessing or even, through suitable servo-mechanisms, controls upstream processes to bring the chemical analysis back within standards.

The present invention solves this problem by, in effect, taking a moving "slice" of a material, such as polymer melt and, while maintaining it at its precise process stream temperature and pressure, passing infrared radiation through it from one side to the other. The maintenance of the process stream temperature requires isolating the sample cell through which the material passes from the very sensitive equipment which characterizes the FTIR type of infrared analysis.

An infrared spectrum is a record of intensity of infrared radiation as a function of frequency or wavelength. A large number of variables affect infrared detection, including atmospheric absorption, a variation of source intensity with frequency, and changing dispersion in the spectrometer in the presence of contaminating substances in the environment. For this reason, the electrical output of an infrared detector is not constant even in situations where the sample is theoretically completely transparent.

To correct for these variations, it is necessary to determine two spectra—one with the sample in the radiation beam and one with the sample removed from the beam. The absorbtion as a function of frequency is then computed from these two spectra. In effect, the spectra with the sample removed from the beam is subtracted from the sample in the beam to leave a resulting spectroscopic "fingerprint" of the substance being examined. Typically, this is done by introducing a second optical path called a reference path which is ideally as nearly like the first beam as possible except for the absence of the sample. In laboratory analysis, this is a simple matter since the environment is controlled expressly because such analysis is taking place.

However, in analyzing materials such as molten polymer within a process stream, the sample must be placed within an oven which maintains the sample at the process stream temperature for analysis. Heretofore, the background or reference sample has been either not taken at all, or taken outside the environment of the sample cell. This produces variations and distortions into the process which result in a less than fully accurate infrared spectrum of the sample material.

SUMMARY OF THE INVENTION

Therefore, it is an object of the invention to provide a spectrophotometric apparatus and method which permits accurate compensation for background radiation absorbtion when analyzing materials in a moving process stream.

It is another object of the invention to provide an apparatus and method which permits the creation of a reference radiation path within an environment similar to the environment of the material being analyzed.

It is another object of the invention to permit a reference radiation spectra to be determined on an on-line basis when desired during the analysis of the material in the sample cell.

These and other objects of the present invention are achieved in the preferred embodiments disclosed below by providing an apparatus for spectrophotometric analysis of material in a moving process stream wherein the material is directed into an observation chamber within a sample cell and exposed to a radiation beam suitable for spectrophotometric purposes. The apparatus comprises a radiation source and a radiation detector contained within a first compartment and a second compartment environmentally isolated from the first compartment and within which the sample cell is contained.

Reflective means are positioned within the second compartment for receiving the radiation beam from the first compartment, directing the radiation beam through the sample cell and the material to be analyzed contained therein, and directing the radiation beam back into the second compartment and the radiation detector positioned therein.

The second compartment contains means for maintaining the environment therein within a range acceptable for radiation analysis of the material within the sample cell. Reference means are positioned within the second compartment for diverting the radiation beam from passage through the material and for determining a reference spectra within the same environment as the sample cell and directing the diverted beam to the radiation detector.

According to one preferred embodiment of the invention, the reflective means comprises at least first and second primary mirrors, the first primary mirror positioned upstream of the sample cell for directing the radiation beam into through the sample cell and the second primary mirror positioned downstream of the sample cell for directing the radiation beam away from the sample cell and towards the first compartment and the radiation detector positioned therein.

According to another preferred embodiment of the invention, the reflective means comprises at least first and second primary mirrors, the first primary mirror positioned upstream of the sample cell for directing the radiation beam into and through the sample cell and the second primary mirror positioned downstream of the sample cell for directing the radiation beam away from the sample cell and towards the first compartment and the radiation detector positioned therein. The reference means comprises a secondary mirror upstream of the sample cell for diverting the radiation beam to the downstream side of the sample cell through the environment of the second compartment without passing through the material in the sample cell.

According to yet another embodiment of the invention, the reflective means comprises at least first and second primary mirrors, the first primary mirror positioned upstream of the sample cell for directing the radiation beam into and through the sample cell and the second primary mirror positioned downstream of the sample cell for directing the radiation beam away from the sample cell and towards the first compartment and the radiation detector positioned therein. The reference means comprises a first secondary mirror upstream of the sample cell for diverting the radiation beam to the downstream side of the sample cell through the environment of the second compartment without passing through the material in the sample cell and a second secondary mirror downstream of the sample cell for receiving the radiation beam reflected by the first secondary mirror and directing the radiation beam out of the second compartment.

Preferably, the apparatus comprises an FTIR system.

According to one preferred embodiment of the invention, each secondary mirror includes pivot means for pivoting the secondary mirror into the radiation beam path when a reference spectra is desired.

In accordance with the method of spectrophotometric analysis of material in a moving process stream according to the invention, the material is directed into an observation chamber within a sample cell and exposed to a radiation beam suitable for spectrophotometric purposes. The method includes the steps of providing a radiation source and a radiation detector contained within a first compartment and a second compartment environmentally isolated from the first compartment and within which the sample cell is contained. Reflective means are positioned within the second compartment for receiving the radiation beam from the first compartment, directing the radiation beam through the sample cell and the material to be analyzed contained therein, and directing the radiation beam back into the second compartment and the radiation detector positioned therein.

The environment within the second compartment is maintained within a range acceptable for radiation analysis of the material within the sample cell.

The radiation beam is diverted from passage through the material while continuing the passage of the beam through the environment of the second compartment and is directed to the radiation detector.

A reference spectra is thereby determined within the same environment as the sample cell.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIG. 4 is a cross-section of a pair of the retainers shown in FIG. 3 in operating position;

FIG. 5 is a vertical cross-section, with parts omitted for clarity, showing the valving arrangement and observation chamber of the sample cell;

FIG. 6 is a horizontal cross-section of the sample cell shown in FIG. 5, with parts omitted for clarity, showing the valving arrangement and the observation chamber of the invention;

DESCRIPTION OF THE PREFERRED EMBODIMENT

Figure 1:
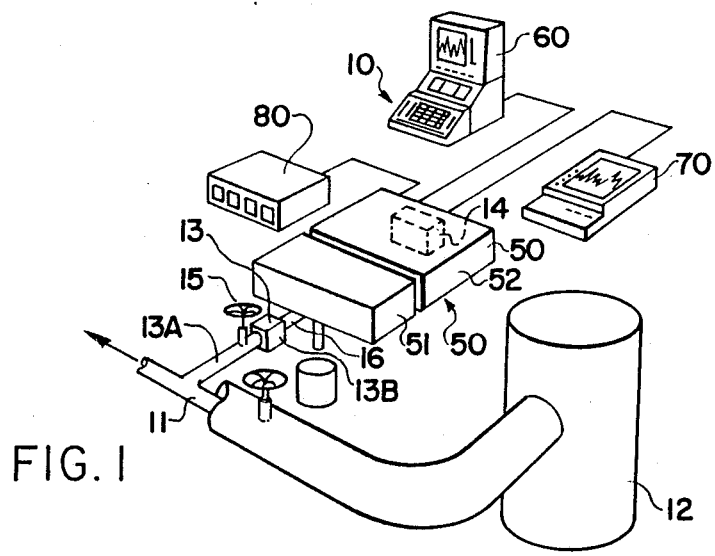
FIG. 1 is a schematic view of the spectrophotoscopic apparatus which includes the invention according to the application, in communication with a process stream.

Referring now specifically to the drawings, a spectrophotometric apparatus according to the present invention is broadly illustrated in FIG. 1 at broad reference numeral 10. Apparatus 10 samples a material moving in a process stream 11. For the purposes of description of the invention, the material in the process stream is considered to be polymer melt which is flowing downstream of a source such as a reaction vessel 12 where the polymer is created. Of course, in other environments the upstream source may be a heated vessel where polymer in chip, pellet or flake form manufactured elsewhere is reheated to its melted state for further processing. Polymer melt is diverted from the process stream 11 through a feeder line 13 which is contained within an insulated jacket 13A to maintain the polymer melt at its process stream temperature. Flow to feeder line 13 may be controlled by a feed pump 13B and a gate valve 15. Polymer melt flows from feeder line 13 into a sample cell 14 according to the present invention. The sample is analyzed by infrared radiation by means of a FTIR spectrometer 50. The analysis process is controlled by a computer 60 which also displays the infrared spectra generated by the analysis of the polymer melt. The analysis shown on the display terminal of the computer 60 can be obtained in hard copy form from a plotter 70. The temperature of the polymer melt within sample cell 14 is controlled by a temperature regulator 80.

Spectrometer 50 is contained within a spectrometer compartment 51 which is connected for radiation transmission with a sample cell compartment 52 within which sample cell 14 is positioned.

Figure 2:
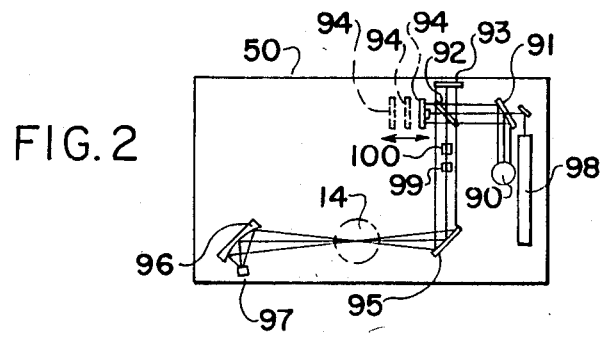
FIG. 2 is a schematic of a Fourier Transform infrared spectrometer with a Michelson interferometer used in connection with the sample cell according to an embodiment of this invention.

The Fourier Transform Infrared (FTIR) spectrometer 50 is illustrated in further detail in FIG. 2. An infrared radiation source 90 is reflected at right angles off a mirror 91 and through a beam splitter 92. Fifty percent of the infrared light is reflected to a fixed mirror 93 and 50 percent of the light is transmitted to a moving mirror 94. The fixed mirror 93 returns the infrared radiation by reflection back to the beam splitter along a fixed optical path. The moving mirror 94 reflects radiation back at pathlengths that are variable and thus may differ from the fixed mirror. The reflected beams then recombine at the beam splitter 92 and a portion of this recombined beam is directed to a focusing lens 95. Lens 95 directs the converging infrared beam to a focus point within sample cell 14 (shown schematically) where the infrared beam again diverges. The beam is reflected again by a focusing lens 96 to an infrared detector 97. A laser 98 is used to measure the change in optical path difference within spectrometer 50. The laser 98 emits a beam with a very precise interference pattern which yields an interferogram which is a cosine wave. This cosine wave triggers the digitization of the detector signal. Spectrometer 50 also includes a laser detector 99 and a white light detector 100.

Spectrometer 50 is very susceptible to heat. Since, as described below, the polymer melt must be maintained at its process stream temperature, sample cell 14 is positioned within sample cell compartment 52 and prevents heat from sample cell 14 from damaging the components of spectrometer 50 within the compartment 51.

Referring now to FIGS. 5 and 6, sample cell 14 is described in detail. The core of sample cell 15 is a steel block 18 into which is formed an inlet conduit 19A and an outlet conduit 19B. Conduits 19A, 19B are collectively, substantially U-shaped and begin at a threaded inlet 20 which connects with feeder line 13 and ends at an outlet 21 directly beneath inlet 20 which discharges polymer melt into a discharge line 16.

A threaded temperature sample valve access port 33 is formed in block 18 and communicates with conduit 19.

A plug valve 34 having mating threads thereon is positioned in sample valve access port 33 and is movable between positions wherein polymer melt is permitted to flow into the observation zone and a closed position at which flow to the observation zone is not permitted. A bypass valve access port 35 is formed in block 18 and also communicates with conduit 19B. A bypass plug valve 36 with mating threads thereon is positioned in bypass access port 35 and is movable between open and closed positions. A threaded retainer bore 37 is formed in and extends through block 18 from one side to the other. A threaded retainer 38 is positioned in bore 37 from one side and a like threaded retainer 39 is positioned in bore 37 from the other side.

As is best shown in FIG. 4, retainers 38 and 39 have tapered apertures 38A and 39A, respectively, extending through them from one end to the other. An annular shoulder recess 38B is formed in one end of recess 38 and an annular recess 39B is formed in one end of retainer 39. Disk-shaped crystals 40 of an infrared transmissible substance such as zinc selinide (ZnSe) are fixedly secured into recesses 38B and 39B by a high temperature adhesive such as epoxy cement. The crystals 40 form "windows" through which infrared radiation is directed. Note that crystals 40, which for example are 0.72 in. (18 mm) in diameter and 0.16 in. (4 mm) thick are supported on virtually their entire surface area by retainers 38 and 39, respectively, with only a central exposed aperture of 0.32 in. (8 mm) diameter allowing for the transmission of radiation. This permits crystals 40 to withstand very high temperature and pressure.

Figure 3:
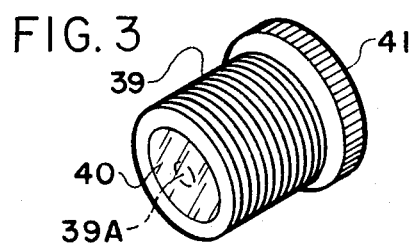
FIG. 3 is a perspective view of a window retainer in accordance with the invention.

As shown in FIGS. 3 and 4, retainers 38 and 39 include on the ends opposite crystal 40 a threaded drive gear 41 in encircling relation to apertures 38A, 39A, respectively. Stepper motors 44 and 45 engage gears 41 and permit crystals 40 to be moved relative to each other.

As is shown in FIGS. 5 and 6, bore 37 intersects inlet conduit 19A downstream of sample valve access port 33. Retainers 38 and 39 are positioned in bore 37 in closely spaced-apart relation. The space between crystals 40 in retainers 38 and 39 define an observation chamber 42. As polymer melt flows from inlet conduit 19A into and through observation chamber 42, it is exposed to the transmission of infrared radiation through it from one side to the other.

With sample valve 34 in the open position, the polymer melt flows between crystals 40 of retainers 38 and 39, forming an extremely thin sample of polymer through which infrared radiation is transmitted from one side of the sample to the other. Stepper motors 44, 45 permit the width of the observation chamber 43 to be precisely adjusted to the exact distance required to obtain the most accurate results. Stepper motors 44, 45 can be programed through computer 60 to adjust the width of the observation chamber to the exact width necessary for a given sample procedure and can operate in unison to keep the configuration of the observation chamber symmetric, or can operate singly. Of course, when symmetric operation is unnecessary, only one stepper motor need be provided.

The polymer melt continues downstream into outlet conduit 19B and exits through discharge outlet 21 into discharge line 16.

It has been determined that the residence time of the polymer in the sample cell 14 can be greatly reduced by enlarging the diameter of the outlet conduit 19B in relation to the diameter of the inlet conduit 19A. A 40% increase in diameter significantly reduces the pressure in the sample cell 14 and yet permits the polymer to move through the inlet conduit 19A much more quickly. Of course the flow rate in outlet conduit 19B is less than in the inlet conduit 19A. However, once the polymer has been subjected to infrared analysis, residence time is a less important factor. Reduced residence time in sample cell 14 permits a more accurate analysis by testing the material before degradation begins.

The polymer melt may be discarded or reintroduced back into the process stream 11, as desired.

If sampling is not carried on continuously, sample valve 34 is closed and bypass valve 36 is opened at predetermined intervals. In this configuration, the polymer melt is blocked from entering observation chamber 42 and instead passes through bypass valve access port 35 into conduit 19B upstream of observation chamber 42 and out through discharge outlet 21, as described above.

There is a third possibility for routing polymer melt through block 18. This involves having sample valve 34 and bypass valve 36 both open to a predetermined extent. This would most usually be done when continuous sampling is desired. In this procedure, sample valve 34 is opened sufficiently so that, for example, approximately 10 percent of the polymer melt in inlet conduit 19A flows past sample valve 34 and into observation chamber 42. Bypass valve 36 is opened to a considerably greater extent so that the remaining 90 percent of the polymer melt bypasses observation chamber 42 and exits through discharge outlet 21. By regulating sample valve 34 and bypass valve 36 relative to each other, the percentage of the polymer melt in inlet conduit 19A which is sampled and analyzed in observation chamber 42 can be varied to obtain a more rapid sample.

The use of the sample cell 14 above permits accurate spectrophotometric analysis of a material within a process stream. In addition to the use of infrared radiation, radiation in the visible, ultraviolet and other spectra can be used. One major advantage of the sample cell 14 is that the sample is taken and analyzed in a noninvasive manner, as distinguished from the invasive probe known in the prior art.

Consistent with the significant temperatures and pressures to which sample cell 14 may be exposed, its primary components are constructed of high-grade stainless steel. All of the conduits are polished, as are the machine threads. In addition, the threads can be wrapped with Teflon tape. No brass, copper or other material which might react with the material being analyzed is used.

A pressure transducer, not shown in the drawings, may be provided to monitor pressure within inlet conduit 19A.

Figure 7:
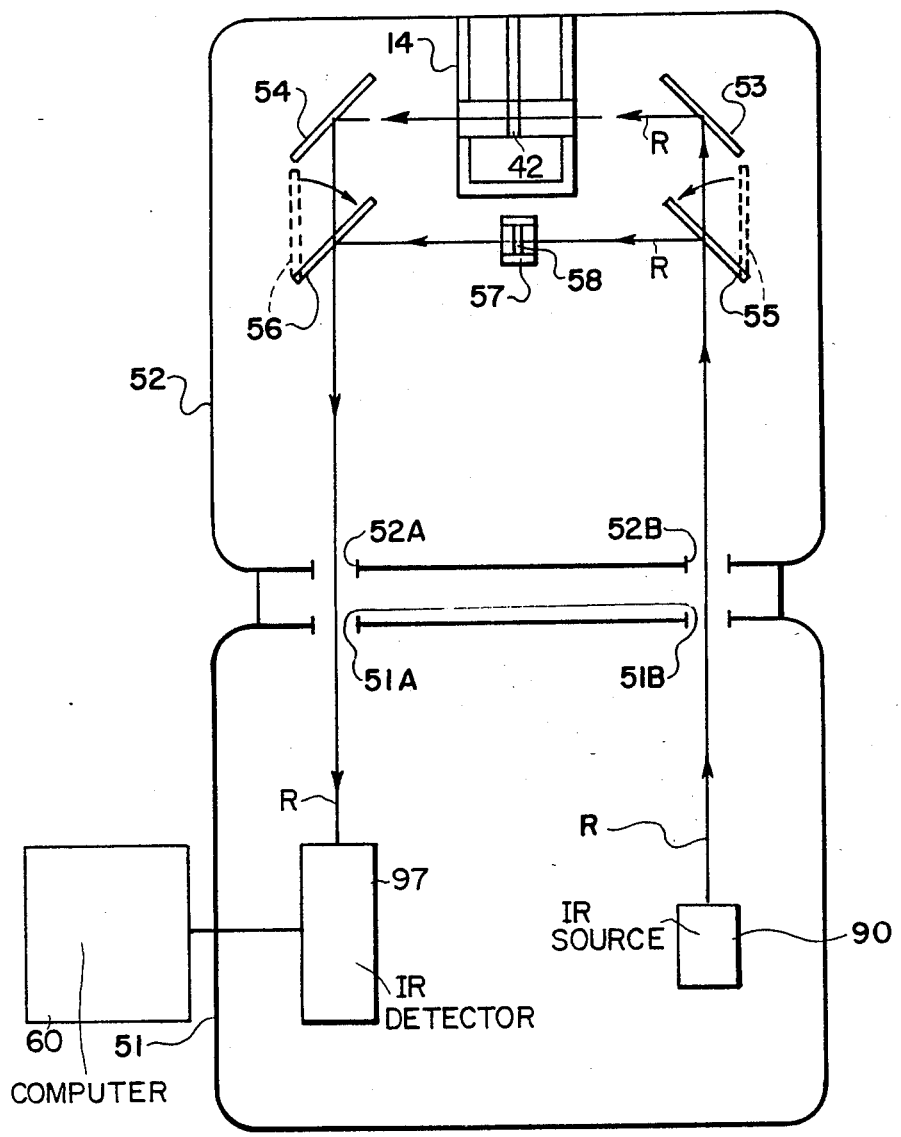
FIG. 7 is a schematic plan view of a spectrometer according to one embodiment of the invention.

Referring now to FIG. 7, the construction of the compartments within which the FTIR equipment and the sample cell 14 are contained is described. Compartment 51 is rigidly but removably connected with the sample cell compartment 52. The adjacent walls of compartments 51 and 52 are provided with aligned openings 51A, 51B, 52A and 52B so that a radiation beam "R" from the radiation source 90 can enter sample cell compartment 52, pass through sample cell 14 and reenter compartment 51. The two compartments are attached by air-tight fittings so that atmospheric contaminants can be purged from the sampling environment.

A pair of primary mirrors 53 and 54 are provided which deflect the radiation at right angles from its path into compartment 52 into and through sample cell 14 from one side to the other and back into compartment 51. In addition, two secondary mirrors 55 and 56 are pivotally mounted to move between a retracted position (shown in phantom lines) and a beam-diverting position in which the radiation beam is diverted from its passage through the sample cell 14 and through a reference sample holder 57. The ability to divert the radiation beam in this manner has a significant effect on the accuracy of the infrared analysis.

Before carrying out a sampling procedure of the material in the sample cell 14—for example, polymer melt—, the entire system is calibrated by directing the radiation of beam "R" through the sample holder 57. For this purpose the sample holder is empty, so that the beam "R" is merely passing through the atmosphere within the sample cell compartment 52, thereby taking a "background" reading which can be subtracted from the sample cell 14 reading to arrive at an accurate test result. The "subtraction" takes place by storing the results of the background reading in computer 60, which is programmed to do all of the necessary FTIR computations. The background reading detects and compensates for thermal expansion of the hardware, temperature variations, the presence of volatiles and water vapor within the sample cell compartment 52, and, in short, all detectable variations between the atmosphere in the compartment 51 and the sample cell compartment 52. The diversion of the beam by mirrors 55 and 56 takes only a few seconds and can be repeated as frequently as the circumstances require.

Other calibrations can be made by placing a sample of a standard reference material, such as a film 58 of known properties, into the sample holder 57. These properties are detected and stored in computer 60 where a comparison is made with the normal standard and adjustments, if necessary, entered.

Figure 8:
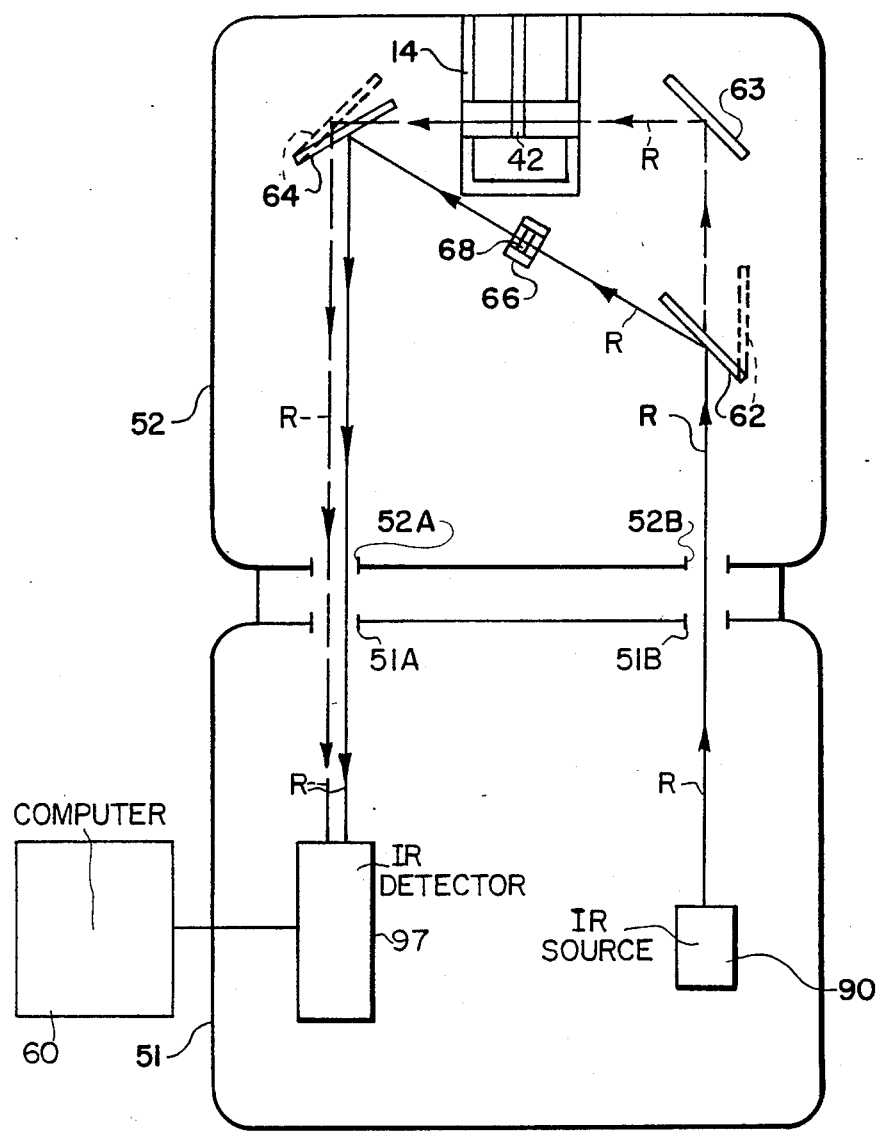
FIG. 8 is a schematic plan view of the sample cell enclosure compartment portion of the spectrometer according to another embodiment of the invention.

As is shown in FIG. 8, the background sample can be taken by use of various mechanical means. In FIG. 8, a single secondary mirror 62 is pivotally mounted in the path of beam "R" upstream of sample cell 14 and a primary mirror 63. A primary mirror 64 downstream of the sample cell 14 is pivoted whereby beam "R" reflected off of secondary mirror 64 is reflected back into compartment 51 off of primary mirror 64 while in the position shown in solid lines. A sample holder 66 is positioned between secondary mirror 62 and primary mirror 64 (in their solid line positions) on a line defined by the beam "R." The advantage of the arrangement shown in FIG. 8 is that the distance traveled by the beam while taking a background sample more closely approximates the distance traveled while sampling through sample cell 14. As described above with reference to FIG. 7, a reference sample, such as a film 68 may be placed in the sample holder 66 as a means of calibrating the system.

A sample cell for the chemical analysis of a material in a moving process stream by spectrophotometric means is described above. Various details of the invention may be changed without departing from its scope. Furthermore, the foregoing description of a preferred embodiment of a sample cell according to the present invention is provided for the purpose of illustration only and not for the purpose of limitation—the invention being defined by the claims.

I claim:

1. An apparatus for spectrophotometric analysis of material in a moving process stream wherein the material is directed into an observation chamber within a sample cell and exposed to a radiation beam suitable for spectrophotometric purposes, said apparatus comprising:
   (a) a radiation source and a radiation detector contained within a first compartment;
   (b) a second compartment environmentally isolated from said first compartment and within which said sample cell is contained;
   (c) reflective means positioned within said second compartment for receiving the radiation beam from said first compartment, directing said radiation beam through said sample cell and the material to be analyzed contained therein, and directing the radiation beam back into the second compartment and the radiation detector positioned therein;
   (d) said second compartment containing means for maintaining the environment therein within a range acceptable for radiation analysis of the material within the sample cell; and
   (e) reference means positioned within said second compartment for diverting said radiation beam from passage through said material and for determining a reference spectra within the same environment as the sample cell and directing the diverted beam to the radiation detector.

2. An apparatus according to claim 1, wherein said reflective means comprises at least first and second primary mirrors, said first primary mirror positioned upstream of said sample cell for directing said radiation beam into and through said sample cell and said second primary mirror positioned downstream of said sample cell for directing said radiation beam away from the sample cell and towards said first compartment and the radiation detector positioned therein.

3. An apparatus according to claim 1, wherein said reflective means comprises at least first and second primary mirrors, said first primary mirror positioned upstream of said sample cell for directing said radiation beam into and through said sample cell and said second primary mirror positioned downstream of said sample cell for directing said radiation beam away from the sample cell and towards said first compartment and the radiation detector positioned therein, and said reference means comprises a secondary mirror upstream of said sample cell for diverting said radiation beam to the downstream side of the sample cell through the environment of the second compartment without passing through the material in the sample cell.

4. An apparatus according to claim 1, wherein said reflective means comprises at least first and second primary mirrors, said first primary mirror positioned upstream of said sample cell for directing said radiation beam into and through said sample cell and said second primary mirror positioned downstream of said sample cell for directing said radiation beam away from the sample cell and towards said first compartment and the radiation detector positioned therein, and said reference means comprises a first secondary mirror upstream of said sample cell for diverting said radiation beam to the downstream side of the sample cell through the environment of the second compartment without passing through the material in the sample cell and a second secondary mirror downstream of the sample cell for receiving the radiation beam reflected by said first secondary mirror and directing the radiation beam out of the second compartment.

5. An apparatus according to claim 1, 2, 3 or 4, wherein said apparatus comprises a FTIR system.

6. An apparatus according to claim 4, wherein each secondary mirror includes pivot means for pivoting said secondary mirror into the radiation beam path when a reference spectra is desired.

7. A method of spectrophotometric analysis of material in a moving process stream wherein the material is directed into an observation chamber within a sample cell and exposed to a radiation beam suitable for spectrophotometric purposes, said (a) providing a radiation source and a radiation detector contained within a first compartment;

(b) providing a second compartment environmentally isolated from said first compartment and within which said sample cell is contained;

(c) providing reflective means positioned within said second compartment for receiving the radiation beam from said first compartment, directing said radiation beam through said sample cell and the material to be analyzed contained therein, and directing the radiation beam back into the second compartment and the radiation detector positioned therein;

(d) maintaining the environment within said second compartment within a range acceptable for radiation analysis of the material within the sample cell;

(e) diverting said radiation beam from passage through said material while continuing the passage of the beam through the environment of the second compartment;

(f) directing the diverted beam to the radiation detector; and (g) determining a reference spectra within the same environment as the sample cell.

* * * * *